(12) United States Patent
Horan et al.

(10) Patent No.: US 12,730,098 B2
(45) Date of Patent: Sep. 8, 2026

(54) CALIBRATION FLUID COMPRISING PYROGALLOL FOR THE CALIBRATION OF BLOOD GAS, ELECTROLYTE, AND/OR METABOLITE INSTRUMENT OXYGEN SENSOR(S)

(71) Applicant: Siemens Healthcare Diagnostics Inc., Tarrytown, NY (US)

(72) Inventors: Kevin Horan, Raynham, MA (US); Murli Narayan, Norfolk, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 815 days.

(21) Appl. No.: 18/150,442

(22) Filed: Jan. 5, 2023

(65) Prior Publication Data

US 2023/0146071 A1 May 11, 2023

Related U.S. Application Data

(63) Continuation of application No. 16/623,943, filed as application No. PCT/US2018/040554 on Jul. 2, 2018, now abandoned.

(60) Provisional application No. 62/529,525, filed on Jul. 7, 2017.

(51) Int. Cl.
*G01N 33/00* (2006.01)
*G01N 27/416* (2006.01)
*G01N 33/49* (2006.01)

(52) U.S. Cl.
CPC ..... *G01N 33/0006* (2013.01); *G01N 27/4163* (2013.01); *G01N 33/4925* (2013.01); *G01N 2496/70* (2013.01)

(58) Field of Classification Search
CPC .............. A61B 5/1495; A61B 5/14542; A61B 2560/0223; G01N 27/4163; G01N 33/0006; G01N 33/4925; G01N 2496/70
See application file for complete search history.

(56) References Cited

U.S. PATENT DOCUMENTS 4,336,031 A 6/1982 Hopmeier et al.
4,843,013 A 6/1989 Chiang
5,185,263 A * 2/1993 Kroneis ............ G01N 27/4165 73/1.05
5,505,828 A 4/1996 Wong et al.
5,780,302 A 7/1998 Conlon et al.
5,968,329 A 10/1999 Anderson et al.
6,632,675 B1 10/2003 Conlon et al.
7,112,284 B2 9/2006 Shimura et al.
8,158,019 B2 4/2012 Langowski et al.
2003/0062262 A1 * 4/2003 Mansouri ............ G01N 33/492 204/400
2003/0224523 A1 12/2003 Thornberg (Continued)

OTHER PUBLICATIONS

International Search Report and Written Opinion on International Application No. PCT/US2018/040554 dated Sep. 18, 2018.

(Continued)

*Primary Examiner* — Jason M Sims
*Assistant Examiner* — Kyle W. Kretzer

(57) ABSTRACT

Compositions, devices, kits, and methods for calibrating at least one oxygen sensor in a blood gas, electrolyte, and/or metabolite instrument utilizing a calibration fluid comprising a pyrogallol oxygen scavenger.

19 Claims, 1 Drawing Sheet

(56) References Cited

U.S. PATENT DOCUMENTS

2016/0178571 A1* 6/2016 Oh ....................... G01N 33/492
422/82.01

OTHER PUBLICATIONS

European Search Report and Written Opinion of European Application No. 18827550.7 dated Jun. 19, 2020.
EMD Millipore, SIGMA-ALDRICH; "Pyrogallol GR for analysis ACS," Apr. 28, 2017, <http://www.sigmaaldrich.com/catalog/product/mm/100612?lang=en®ion=US>, pp. 1-2.
Doona, et al.; "Kinetics and Mechanism of Pyrogallol Autoxidation: Calibration of the Dynamic Response of an Oxygen Electrode," 1993, International Journal of Chemical Klinetics, vol. 25, 239-247.
Abrash, Henry I.; "The Air Oxidation of 4,6-D1 (2-Phenyl-2-Propyl) Pyrogallol Spectroscopic and Kinetic Studies of the Intermediates," Jan. 1977, Carlsberg Research Communications, vol. 42, pp. 11-25.

* cited by examiner

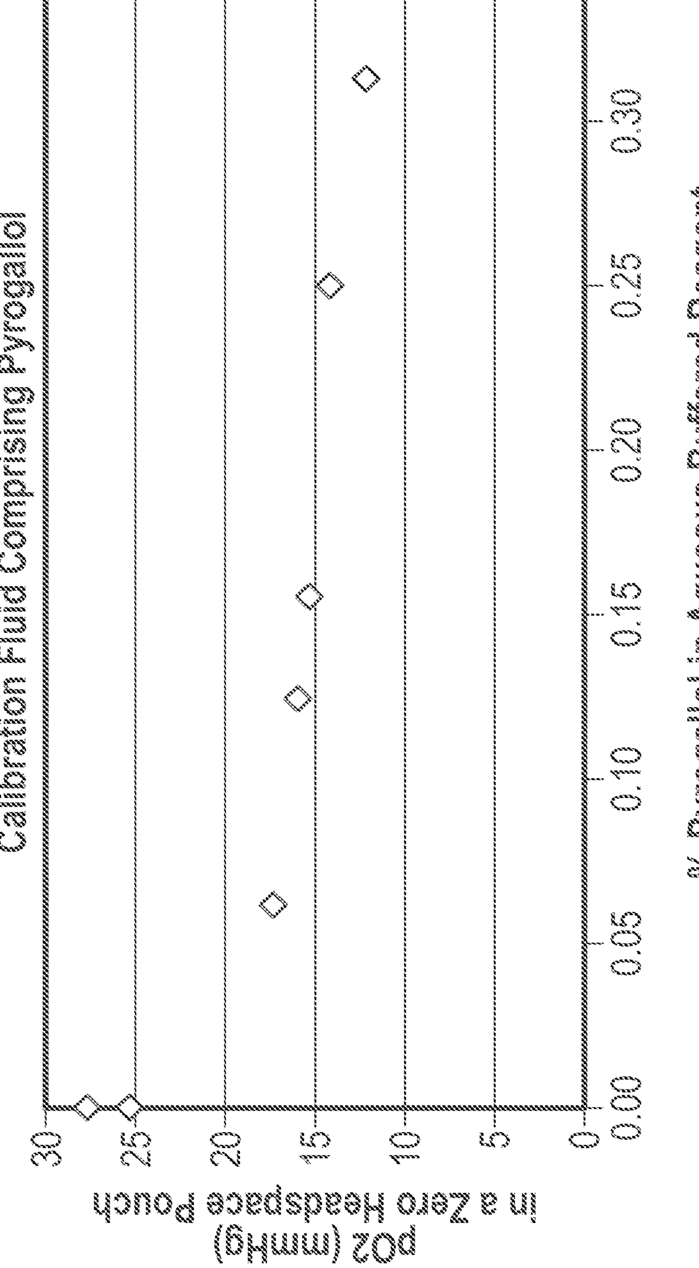
Calibration Fluid Comprising Pyrogallol
pO2 (mmHg)
in a Zero Headspace Pouch
30
25
20
15
10
5
0
0.00
0.05
0.10
0.15
0.20
0.25
0.30
0.35
% Pyrogallol in Aqueous Buffered Reagent

CALIBRATION FLUID COMPRISING PYROGALLOL FOR THE CALIBRATION OF BLOOD GAS, ELECTROLYTE, AND/OR METABOLITE INSTRUMENT OXYGEN SENSOR(S)

REFERENCE TO RELATED APPLICATIONS

The subject application is a continuation of U.S. Ser. No. 16/623,943, filed Dec. 18, 2019, now abandoned; which is a national stage application under 35 USC § 371 of PCT Application No. PCT/US2018/040554, filed Jul. 2, 2018; which claims benefit under 35 USC § 119(e) of U.S. provisional Application No. 62/529,525, filed Jul. 7, 2017. The entire contents of the above-referenced patent applications are hereby expressly incorporated herein by reference.

FEDERALLY FUNDED RESEARCH OR DEVELOPMENT

Not Applicable.

TECHNICAL FIELD

The presently disclosed and claimed inventive concept(s) relate to a compositions(s), device(s), kit(s), and method(s) for calibrating at least one oxygen sensor of a blood gas analyzer system. More specifically, the presently disclosed and claimed inventive concept(s) relate to a calibration fluid comprising pyrogallol for the calibration of at least one oxygen sensor of a blood gas analyzer system.

BACKGROUND OF THE INVENTION

Blood gas analyzers ("BGAs") have been used for years in the medical industry to determine the presence and concentration of certain analytes which may be present in a patient's blood and/or blood sample. BGAs are routinely used by doctors, scientists, researchers, and medical-care professionals to determine the presence and/or concentrations of certain characteristics and/or analytes present in a patient's blood sample, including, without limitation: (1) blood gases (such as pH (acidity), carbon dioxide (measured as $pCO_2$—partial pressure of carbon dioxide), and/or oxygen (measured as $pO_2$—partial pressure of oxygen)); (2) electrolytes (such as sodium ($Na^+$), potassium ($K^+$), Calcium ($Ca^{2+}$), and/or chloride ($Cl^-$); (3) metabolites (such as glucose, lactate, blood urea nitrogen ("BUN"), and/or creatinine); and/or co-oximetry concentration measurements (such as total hemoglobin (tHb), reduced hemoglobin/deoxyhemoglobin (HHb), oxyhemoglobin ($O_2$Hb), saturated oxygen ($SO_2$), carboxyhemoglobin (COHb), methemoglobin (MetHb), fetal hemoglobin (HbF), and/or bilirubin.

When measuring the presence and/or concentration of oxygen present in a patient's blood sample, it is of utmost importance that the oxygen sensor(s) of the blood gas analyzer be properly calibrated—an improperly calibrated oxygen sensor(s) may miscalculate and incorrectly report the actual level(s) of oxygen that is/are present in a patient's blood sample. Calibration of such oxygen sensor(s) (as well as other sensors present in the blood gas analyzer) is/are typically accomplished via routine calibration with at least one calibration fluid. The calibration fluid(s) provide at least a floor measurement of oxygen (i.e., as close to zero (0) millimeters of mercury (mmHg) as possible, with the goal of the floor being zero (0) mmHg) and a predetermined ceiling measurement of oxygen (for instance, by way of example only, 160 mmHg). By using at least the floor and ceiling oxygen measurements, the blood gas analyzer, through algorithmic calculations and circuitry, calibrates the oxygen sensor(s) of the blood gas analyzer to thereby allow for the accurate detection of oxygen in a patient's blood gas sample.

To date, the calibration fluid most widely used to approximate the zero (0) mmHg floor oxygen measurement has been a calibration fluid comprising a combination of sulfite and cobalt as oxygen scavenger reagents. While such oxygen scavenger reagents are effective in setting the floor (i.e., zero (0) mmHg) oxygen measurement for the calibration fluid, there are a number of disadvantages associated with using the sulfite/cobalt calibration fluid. First, cobalt is on the REACH list of banned and/or restricted substances in Europe due to its potential for causing: (1) long-lasting and harmful environmental effects (especially to aquatic life); (2) cancer; and (3) fatalities, if inhaled. In addition, sulfite may have detrimental effects on the functioning of other sensors of the blood gas analyzer (for example, a creatinine sensor, due to the interactions between the sulfite and the creatinine sensor).

In addition, maintaining oxygen levels within reagent bags utilized with BGAs and other types of instrumentation remains a well-known problem in the art because of the oxygen permeability of most polymer-based reagent bag materials. Currently, the primary means to minimize such changes in oxygen levels of liquid reagents is to use a better oxygen barrier material and/or to keep the liquid reagents under low temperature to reduce the kinetic energy of oxygen. While oxygen scavengers have been utilized to confront this problem, the primary sulfite and cobalt oxygen scavengers currently employed suffer from the drawbacks and disadvantages stated herein above.

Accordingly, there is a need for an improved calibration fluid that is both environmentally and medically safe, but which comprises an oxygen scavenging reagent(s), such as pyrogallol, that is effective in setting the floor (i.e., as close to zero (0) mmHg as possible) oxygen measurement(s) of a calibration fluid for use in the calibration of oxygen sensors present in a BGA. It is to such improved compositions, devices, kits, and methods that the presently disclosed and claimed inventive concept(s) is directed.

BRIEF DESCRIPTION OF THE DRAWINGS

FIG. 1 is a graphical representation of a blood gas analyzer calibration fluid comprising various percentages/concentrations of pyrogallol (x-axis) plotted against the partial pressures of oxygen ($pO_2$) produced within a zero-headspace pouch (measured in mmHg) for each particular percentage/concentration of pyrogallol present within the calibration fluid(s) (y-axis).

DETAILED DESCRIPTION

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions, devices, kits, and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The term "circuitry" as used herein includes, but is not limited to, analog and/or digital components, or one or more suitably programmed processors (e.g., microprocessors) and associated hardware and software or hardwired logic. The term "component" may include hardware, such as but not limited to, a processors (e.g., microprocessor), an application specific integrated circuit (ASIC), field programmable gate array (FPGA), a combination of hardware and software, and/or the like. The term "software" as used herein may include one or more computer readable medium (i.e., computer readable instructions) that when executed by one or more components cause the component to perform a specified function. It should be understood that the algorithms described herein may be stored on one or more non-transient memory. Non-limiting exemplary non-transient memory may include random access memory, read only memory, flash memory, and/or the like. Such non-transient memory may be electrically-based, optically-based, and/or the like.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the term "$pO_2$" will be understood to refer to the partial pressure of oxygen, that is, an amount of oxygen in a solution. "$pO_2$" may also be referred to as a level of oxygen dissolved in a solution.

As used herein, the terms "associate" or "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "fluid sample" as used herein will be understood to include any type of biological fluid sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), intestinal fluid, intraperitoneal fluid, pleural fluid, cystic fluid, sweat, interstitial fluid, tears, mucus, urine, bladder wash, semen, combinations, and the like. The typical liquid test sample utilized in accordance with the presently disclosed and/or claimed inventive concept(s) is blood. The volume of the fluid sample utilized in accordance with the presently disclosed and claimed inventive concept(s) can be from about 0.1 to about 300 microliters, or from about 0.5 to about 290 microliters, or from about 1 microliter to about 280 microliters, or from about 2 microliters to about 270 microliters, or from about 5 microliters to about 260 microliters, or from about 10 to about 260 microliters, or from about 15 microliters to about 250 microliters, or from about 20 microliters to about 250 microliters, or from about 30 microliters to about 240 microliters, or from about 40 microliters to about 230 microliters, or from about 50 microliters to about 220 microliters, or from about 60 microliters to about 210 microliters, or from about 70 microliters to about 200 microliters, or from about 80 microliters to about 190 microliters, or from about 90 microliters to about 180 microliters, or from about 100 microliters to about 170 microliters, or from about 110 microliters to about 160 microliters, or from about 120 microliters to about 150 microliters, or from about 130 microliters to about 140 microliters. In one non-limiting embodiment, the volume of the fluid sample is in a range of from about 100 microliters to about 200 microliters.

The term "patient" includes human and veterinary subjects. In certain embodiments, a patient is a mammal. In certain other embodiments, the patient is a human, including, but not limited to, infants, toddlers, children, young adults, adults, and elderly human populations. "Mammal" for purposes of treatment refers to any animal classified as a mammal, including human, domestic and farm animals, nonhuman primates, and zoo, sports, or pet animals, such as dogs, horses, cats, cows, etc.

Turning now to particular embodiments, the presently disclosed and claimed inventive concept(s) relate to a composition(s), device(s), kit(s), and method(s) for calibrating at least one oxygen sensor of a blood gas analyzer system. While a patient's fluid sample is primarily discussed herein in the context of a patient's blood sample, it should be readily understood by a person having ordinary skill in the art that the presently disclosed and/or claimed inventive concepts have applications to all types of a patient's fluid sample. More specifically, the presently disclosed and claimed inventive concept(s) relate to an improved calibration fluid comprising a predetermined amount pyrogallol for the calibration of at least one oxygen sensor of a blood gas analyzer system, as well as devices, kits, and methods of use related thereto.

The presently disclosed and/or claimed inventive concept(s) relate to a method of generating desired oxygen levels for on-board calibration and quality control of at least one oxygen sensor (i.e., $pO_2$ sensor(s)) within a sensor cartridge, including, without limitation, a single-use and/or multiple use sensor cartridge of a blood gas analyzer system. In the method, a calibration (and/or quality control) fluid comprises at least one calibration and/or quality control reagent(s) and an aqueous or solid reagent containing an oxygen scavenger. The oxygen scavenger reduces the amount of dissolved oxygen in the calibration fluid through a chemical reaction in which the oxygen scavenger (i.e., reducing agent) is oxidized by oxygen; the chemical reaction is based on the reaction rate that is affected by the concentrations of the oxygen scavenger and oxygen, the temperature at which the reaction occurs, and the reaction time. By controlling these parameters, the calibration fluid containing the oxygen scavenger achieves the objectives of the presently disclosed and/or claimed inventive concepts, including, but not limited to, setting the floor measurement (i.e., as close to zero (0) mmHg as possible) for the calibration of the at least one oxygen sensor present within the sensor cartridge.

Next, an accurate concentration of the oxygen level in the calibration and/or quality control reagent of the calibration fluid can be calculated. The sensor(s) utilized in accordance with the presently disclosed and/or claimed inventive concept(s) function via amperometry principles, meaning that the sensor(s) of the sensor array detect ions generated in the calibration fluid in response to presence of the analyte(s) of interest. Such ions, when in contact with the electrode(s) of the sensor array, generate an electric current or changes in electric current (typically measured in amperes or nano amperes) which are readily detected and measured by the electrode(s) of the sensor array. The current generated by the electrode(s) of the amperometric sensor array is directly proportional to the concentration of the particular analyte being tested, which, in one embodiment of the presently disclosed and/or claimed inventive concept(s), is oxygen. Amperometry and amperometric sensors are well known in the art and no further discussion is deemed necessary. When pyrogallol is used as the oxygen scavenger, pyrogallol chemically reduces the concentration of oxygen in the calibration fluid (via pyrogallol complexing with the oxygen of the calibration and/or quality control reagent(s)). As the concentration of oxygen is reduced in the calibration fluid, the current measured by the electrode(s) of the amperometric sensor array likewise decreases, the level of decrease being directly proportional to the concentration of oxygen present in the calibration fluid. Accordingly, an accurate concentration of oxygen present in the calibration fluid can then be calculated from the electrochemical current generated (as measured, for instance, in nano amperes) between the amperometric sensor electrode and oxygen present in the calibration fluid (the concentration of oxygen in the calibration fluid being directly proportional to the current generated).

In a closed system, oxygen scavengers, such as pyrogallol, will bind oxygen present in the calibration fluid and lower the level of oxygen present within the calibration fluid. The oxygen level can vary depending on the concentration of oxygen scavenger present, the reaction temperature, and the reaction time. In addition, prior to or after the addition of the oxygen scavenger, the level of oxygen in the calibration fluid can likewise be decreased by pumping out oxygen from the reagent receptacle via a vacuum or via the addition of non-oxygen containing gas(es), including, without limitation, nitrogen and/or carbon dioxide gases.

Compositions utilized in accordance with the presently disclosed and/or claimed inventive concept(s) include calibration and/or quality control reagent(s) and oxygen scavenger-containing reagent(s). When the calibration and/or quality control reagent is brought into contact with the oxygen scavenger, the oxygen scavenger removes oxygen from the calibration and/or quality control reagent(s) (and, as a result, the calibration fluid), thereby providing a desired oxygen level (such as, by way of example only, zero (0) mmHg) in the calibration and/or quality control reagent(s) based on the concentrations of oxygen scavenger(s) and/or calibration/quality control reagent(s) present in the reaction as well as the reaction time and/or temperature at which the reaction occurs.

Any calibration and/or quality control reagent for use in the calibration and/or monitoring of the performance of oxygen sensor(s) of a blood gas analyzer system, such as, by way of example only, RAPIDPoint® 500 Blood Gas Systems commercially offered for sale by Siemens Healthcare Diagnostics, Inc., and for which a desired oxygen concentration must be maintained is encompassed within the scope of the presently disclosed and/or claimed inventive concept(s). In addition to the calibration and/or quality control reagent(s), the calibration fluid may further comprise any other component necessary for functionality thereof, including, but not limited to, inorganic and/or organic salt(s), protein(s), catalyst(s), analyte(s), metabolite(s), and/or gas(es). Such types of calibration and/or quality control reagent(s) are well known in the art, and therefore no further discussion thereof is deemed necessary.

Any oxygen scavenger known in the art and capable of functioning as described or otherwise contemplated herein is encompassed within the scope of the presently disclosed and/or claimed inventive concept(s). Any reducing agent may function as an oxygen scavenger in accordance with the presently disclosed and/or claimed inventive concept(s) as long as the reducing agent is capable of (i) removing dissolved oxygen from an aqueous solution/fluid (i.e., the calibration fluid) and (ii) generating an electrochemically active product capable of being measured by amperometric sensor(s) (i.e., the electrode(s) of the amperometric sensor array of the presently disclosed and/or claimed inventive concept(s)). Examples of oxygen scavengers that may be utilized in accordance with the presently disclosed and/or claimed inventive concept(s) include, but are not limited to, pyrogallol, as well as any combination thereof. However, it should be readily understood to a person having ordinary skill in the art that other oxygen scavengers that are capable of functioning as described or other contemplated herein are encompassed by the presently disclosed and/or claimed inventive concept(s), and, as such, no further discussion thereof is deemed necessary. As discussed herein, in one non-limiting embodiment of the presently disclosed and/or claimed inventive concept(s), the oxygen scavenger is pyrogallol.

Any electrode known in the art and capable of functioning as described or otherwise contemplated herein is encompassed within the scope of the presently disclosed and/or claimed inventive concept(s). That is, any electrode may function as an electrode in accordance with the presently disclosed and/or claimed inventive concept(s) as long as the electrode is electrochemically active and is capable of producing a current(s) in response to exposure to an analyte of interest (which is, in one non-limiting embodiment of the presently disclosed and/or claimed inventive concept(s), oxygen) in a calibration fluid, the current(s) generated being directly proportional to the concentration of the analyte of interest present in the calibration fluid. A non-limiting example of an electrode that may be utilized in accordance with the presently disclosed and/or claimed inventive concept(s) include a bar metal electrode. However, other electrodes that are capable of functioning as described or otherwise contemplated herein after also well known in the art and encompassed by the presently disclosed and/or claimed inventive concept(s), and, therefore, no further discussion thereof is deemed necessary.

Certain embodiments of the presently disclosed and/or claimed inventive concept(s) are directed to kits in which oxygen levels can be controlled (and/or specific oxygen levels can be generated) for calibration and/or quality control fluid(s); in addition, the generated desired oxygen levels (for instance, a calibration fluid comprising an oxygen measurement of about zero (0) mmHg and an oxygen concentration of about zero (0)) can be accurately measured in the kits of these embodiments. The calibration and/or quality control fluid(s) may be used for monitoring the performance of, for example, but not by way of limitation, blood gas (including $pO_2$ measurements of a patient's fluid sample), electrolyte, and/or metabolite instrumentation. The kit includes at least one calibration and/or quality control fluid which comprises: (i) at least one calibration and/or quality control reagent containing oxygen, as described herein above or otherwise contemplated herein; and (2) at least one second reagent that comprises at least one oxygen scavenger. While the oxygen scavenger reagent is primarily discussed herein as being in an aqueous form, it should be readily understood to a person having ordinary skill in the art that the oxygen scavenger-containing reagent may be in lyophilized or solidified form. When use of the calibration fluid is desired, a specific and/or predetermined amount of the second reagent for instance, a pyrogallol oxygen scavenger reagent) is combined with the calibration and/or quality control reagent so that the oxygen scavenger complexes with and reduces the amount of oxygen present in the calibration and/or quality control reagent of the calibration fluid. In this manner, a desired oxygen level can be provided in the calibration and/or quality control fluid immediately before and/or at the time of use of the calibration and/or quality control fluid. In one non-limiting embodiment, the predetermined amount of the second reagent when combined with the calibration and/or quality control reagent is such that the partial pressure of oxygen in the calibration and/or quality control fluid is about zero (0) mmHg following the combination.

The oxygen scavenger may be used at a molar ratio of less than or equal to 1:1 with the oxygen of the calibration and/or quality control reagent of the calibration fluid. A person having ordinary skill in the art would recognize that the resultant concentration of oxygen obtained in the calibration fluids upon exposure of the calibration and/or quality control reagent(s) to the oxygen scavenger is directly related to: (i) the initial concentration of oxygen in the calibration and/or quality control reagent(s) of the calibration fluid; (ii) initial the concentration of oxygen scavenger; (iii) the amount of time that the oxygen scavenger-containing reagent(s) is/are allowed to come into contact with the calibration and/or quality control reagent; and/or (iv) the temperature at which the reaction occurs. For example, but not by way of limitation, it may be desired in the calibration fluid to utilize a molar ratio of oxygen scavenger:oxygen in the calibration/ quality control reagent of about 0.001:1, about 0.002:1, about 0.003:1, about 0.004:1, about 0.005:1, about 0.006:1, about 0.007:1, about 0.008:1, about 0.009:1, about 0.01:1, about 0.02:1, about 0.03:1, about 0.04:1, about 0.05:1, about 0.06:1, about 0.07:1, about 0.08:1, about 0.09:1, about 0.1:1, about 0.15:1, about 0.2:1, about 0.25:1, about 0.3:1, about 0.35:1, about 0.4:1, about 0.45:1, about 0.5:1, about 0.55:1, about 0.6:1, about 0.65:1, about 0.7:1, about 0.75:1, about 0.8:1, about 0.85:1, about 0.9:1, about 0.95:1, and about 1:1. Alternatively, it may be desired to utilize a molar ratio of oxygen scavenger:oxygen in the calibration/quality control reagent in a range of any of the above values (i.e., a range of from about 0.1:1 to about 1:1, or about 0.3:1 to about 0.9:1, etc.), and therefore any range formed from the combination of two values listed above is also encompassed within the scope of the presently disclosed and/or claimed inventive concept(s). In one non-limiting embodiment, the concentration of the oxygen scavenger (such as, by way of example only, pyrogallol) in the calibration fluid is from about 0.05% to about 0.5%.

The reaction time may be any amount of time that allows for the oxygen scavenger-containing reagent to complex with oxygen in the calibration and/or quality control reagent and that is suitable for use with the methods and devices disclosed or otherwise contemplated herein. For example, but not by way of limitation, the reaction time may be about 0.001 second, about 0.002 second, about 0.003 second, about 0.004 second, about 0.005 second, about 0.006 second, about 0.007 second, about 0.008 second, about 0.009 second, about 0.01 second, about 0.05 second, about 0.1 second, about 0.15 second, about 0.2 second, about 0.25 second, about 0.3 second, about 0.35 second, about 0.4 second, about 0.45 second, about 0.5 second, about 0.55 second, about 0.6 second, about 0.65 second, about 0.7 second, about 0.75 second, about 0.8 second, about 0.85 second, about 0.9 second, about 0.95 second, about 1 second, about 2 seconds, about 3 seconds, about 4 seconds, about 5 seconds, about 6 seconds, about 7 seconds, about 8 seconds, about 9 seconds, about 10 seconds, about 11 seconds, about 12 seconds, about 13 seconds, about 14 seconds, about 15 seconds, about 16 seconds, about 17 seconds, about 18 seconds, about 19 seconds, about 20 seconds, about 25 seconds, about 30 seconds, about 35 seconds, about 40 seconds, about 45 seconds, about 50 seconds, about 55 seconds, about 60 seconds, about 65 seconds, about 70 seconds, about 75 seconds, about 80 seconds, about 85 seconds, about 90 seconds, about 95 seconds, about 100 seconds, about 105 seconds, about 110 seconds, about 115 seconds, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 25 minutes, about 30 minutes, about 35 minutes, about 40 minutes, about 45 minutes, about 50 minutes, about 55 minutes, about 60 minutes, and the like. Alternatively, it may be desired to utilize a reaction time within a range of any of the above values (i.e., a range of from about 0.01 second to about 20 minutes, or about 1 second to about 10 seconds, etc.), and therefore any range formed from the combination of two values listed above is also encompassed within the scope of the presently disclosed and/or claimed inventive concept(s). In addition, in one non-limiting embodiment, the oxygen sensor(s) of the blood gas analyzer system is calibrated at intervals of time ranging from about 20 minutes to about 120 minutes. In one non-limiting embodiment, the calibration of the at least one sensor (for instance, the at least one $pO_2$ sensor) occurs within 30 seconds following the formation of the calibration fluid.

Any reaction temperature known in the art may be utilized in accordance with the presently disclosed and/or claimed inventive concept(s) so long as the complexation of oxygen by the oxygen scavenger will occur at that temperature, and as long as the temperature is suitable for use with the methods and devices disclosed or otherwise contemplated herein. For example, but not by way of limitation, the reaction temperature may be about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., and the like. Alternatively, it may be desired to utilize a reaction temperature within a range of any of the above values (i.e., a range of from about 4° C. to about 37° C., or about 20° C. to about 26° C., etc.), and therefore any range formed from the combination of two values listed above is also encompassed within the scope of the presently disclosed and/or claimed inventive concept(s).

In certain embodiments, the calibration and/or quality control reagent(s) and/or oxygen scavenger-containing reagent(s) comprising the calibration fluid present in the kit may be aliquoted into single units thereof, or the kit may contain a volume of each reagent that constitutes multiple units thereof.

The calibration and/or quality control reagent(s) and/or oxygen scavenger-containing reagent(s) may be disposed in the kit in any form known in the art that allows the reagents to function in accordance with the presently disclosed and/or claimed inventive concept(s). For example, but not by way of limitation, the reagent(s) may be in aqueous solution, lyophilized and/or solidified. When the reagent(s) are lyophilized and/or solidified, the reagents(s) may be disposed in the kit in any form, including, but not limited to, a bead, a hemisphere, a cake, a tablet, or any other form, as well as any combination of these or other types of forms. In addition, the calibration and/or quality control reagent and/or the oxygen scavenger-containing reagent may also be maintained in a substantially air tight environment until use thereof, including, without limitation, at least one air tight bag, container, bottle, ampule, and/or combinations thereof. In one non-limiting embodiment, the calibration and/or quality control reagent and/or oxygen scavenger may be maintained and/or contained within an air tight, flexible package, such as the air tight, flexible package described and/or claimed in U.S. Pat. No. 5,780,302, the contents of which is expressly incorporated in its entirety by reference.

The kit may further include a sensor array that includes at least one electrode capable of producing a current(s) in response to exposure to an analyte of interest (which is, in one non-limiting embodiment of the presently disclosed and/or claimed inventive concept(s), oxygen) in a calibration fluid, the current(s) generated being directly proportional to the concentration of the analyte of interest present in the calibration fluid. In certain non-limiting embodiments, the sensor array may further comprise a $pO_2$ sensor(s) with which the calibration fluid is used.

Certain embodiments of the presently disclosed and/or claimed inventive concept(s) are also directed to methods of controlling an oxygen level (and/or generating a desired oxygen level, for instance, an oxygen level of zero (0) mmHg) in a calibration fluid used in monitoring the performance of, for example, blood gas, electrolyte, and/or metabolite instrumentation. In the method, the oxygen level of the calibration fluid as described in detail herein above or otherwise contemplated therein is controlled by exposure to any of the oxygen scavenger-containing reagents described in detail herein above or otherwise contemplated herein, wherein the oxygen scavenger-containing reagent complexes with a specific amount of oxygen in the calibration and/or quality control reagent(s) and thereby provides a desired level of oxygen in the calibration fluid at the time of use. The calibration fluid containing the desired oxygen level is then used to monitor the performance of blood gas, electrolyte, and/or metabolite instrumentation, and the reagent contains a desired oxygen level (for instance, by way of example only, an oxygen level of zero (0) mmHg) based upon the concentration of the oxygen scavenger and the reaction time and reaction temperature of the exposure.

A person of ordinary skill in the art would recognize that the amount of oxygen complexed by the oxygen scavenger is directly related to the amount of oxygen scavenger that is allowed to come into contact with the calibration and/or quality control reagent as well as the time and temperature at which the reaction occurs. The exposure is performed at a specific reaction temperature and for a specific amount of time (as described in detail herein above and/or otherwise contemplated herein) and may occur immediately prior to the use of the calibration fluid.

Certain embodiments of the method also include accurately measuring the oxygen level so generated. By way of example, and not by way of limitation, when pyrogallol is used as the oxygen scavenger, pyrogallol chemically reduces the concentration of oxygen in the calibration fluid (via pyrogallol complexing with the oxygen of the calibration and/or quality control reagent(s)). As the concentration of oxygen is reduced in the calibration fluid, the current measured by the electrode(s) of the amperometric sensor array likewise decreases, the level of decrease being directly proportional to the concentration of oxygen present in the calibration fluid. Accordingly, an accurate concentration of oxygen present in the calibration fluid can be calculated from the electrochemical current(s) generated (as measured, for instance, in nano amperes) between the amperometric oxygen sensor array electrode and oxygen present in the calibration fluid.

The presently disclosed and/or claimed inventive concept(s) is additionally directed to a device capable of controlling an oxygen level (and/or generating different oxygen levels) in a calibration and/or quality control reagent for monitoring the performance of, for example, blood gas, electrolyte, and/or metabolite instrumentation; the device may also be capable of accurately measuring the oxygen level so generated. In certain non-limiting embodiments, the device is a sensor cartridge, such as but not limited to, a single-use sensor cartridge and/or a multiple-use sensor cartridge. The device includes any of the calibration and/or quality control reagents comprising oxygen described in detail herein above, as well as any of the oxygen scavenger-containing reagents as described in detail herein above. As described in detail herein above, a person of ordinary skill in the art would recognize that the amount of oxygen removed from the calibration and/or quality control reagent is directly related to the amount of oxygen scavenger that is allowed to come into contact with the calibration and/or quality control reagent as well as the time and temperature at which the reaction occurs.

The device may further include a sensor array, wherein the sensor array includes a sensor (such as, but not limited to, a $pO_2$ sensor) and an electrode. Once the desired oxygen level is generated, the oxygen level so generated can be accurately measured using the electrode; for instance, by way of example only, when pyrogallol is used as the oxygen scavenger, pyrogallol chemically reduces the concentration of oxygen in the calibration fluid (via pyrogallol complexing with the oxygen of the of the calibration and/or quality control reagent(s)). As the concentration of oxygen is reduced in the calibration fluid, the current measured by the electrode(s) of the amperometric sensor array likewise decreases, the level of decrease being directly proportional to the concentration of oxygen present in the calibration fluid. Accordingly, an accurate concentration of oxygen present in the calibration fluid is calculated from the electrochemical current generated (as measured, for instance, in nano amperes) between the electrode(s) of the amperometric sensor array and oxygen present in the calibration fluid. Next, the calibration fluid can be brought into contact with the sensor(s) of the sensor array, such as but not limited to a $pO_2$ sensor(s), thus allowing for calibration of the sensor.

The presently disclosed and/or claimed inventive concept(s) is also directed to a method for monitoring the performance of blood gas, electrolyte, and/or metabolite instrumentation. In the method, any of the devices described herein above or otherwise contemplated herein is disposed into a blood gas, electrolyte, and/or metabolite instrumentation, and the device is activated at a certain temperature and for a certain period of time to provide a desired oxygen level for the calibration and/or quality control reagent. The reagent containing the desired oxygen level is then brought into contact with a $pO_2$ sensor for calibration and/or quality control of the blood gas, electrolyte, and/or metabolite instrument. In one non-limiting embodiment, the desired oxygen level is about zero (0) mmHg.

In certain embodiments of the method, the oxygen level generated in the calibration and/or quality control reagent upon activation of the device is accurately measured. For instance, by way of example only, when pyrogallol is used as the oxygen scavenger, pyrogallol chemically reduces the concentration of oxygen in the calibration fluid (via pyrogallol complexing with the oxygen of the calibration and/or quality control reagent(s)). As the concentration of oxygen is reduced in the calibration fluid, the current measured by the electrode(s) of the amperometric sensor array likewise decreases, the level of decrease being directly proportional to the concentration of oxygen present in the calibration fluid. Accordingly, an accurate concentration of oxygen present in the calibration fluid is calculated from the electrochemical current generated (as measured, for instance, in nano amperes) between the electrode(s) of the amperometric sensor array and oxygen present in the calibration fluid.

The various embodiments of compositions, kits, devices, and methods of the presently disclosed and/or claimed inventive concept(s) may be utilized with any blood gas, electrolyte, and/or metabolite instrument (for instance, RAPIDPoint® 500 Blood Gas Systems commercially offered by Siemens Healthcare Diagnostics, Inc.) for which calibration and/or quality control is desired. In certain, non-limiting embodiments, the instrument may be a point of care instrument. The blood gas, electrolyte, and/or metabolite instrument may be a system or systems that are able to embody and/or execute the logic of the methods/processes described herein. Logic embodied in the form of software instructions and/or firmware may be executed on any appropriate hardware. For example, logic embodied in the form of software instructions and/or firmware may be executed by one or more components on a dedicated system or systems, on a personal computer system, on a distributed processing computer system, and/or the like. In some embodiments, the entire logic may be implemented in a stand-alone environment operating on an instrument (such as, but not limited to, a point of care instrument). In other embodiments, the logic may be implemented in a networked environment such as a distributed system in which multiple instruments collect data that is transmitted to a centralized computer system for analyzing the data and supplying the results of the analysis to the instruments. Each element of the instrument may be partially or completely network-based or cloud based, and may or may not be located in a single physical location.

Thus, in accordance with the presently disclosed and/or claimed inventive concept(s), there have been provided compositions, kits, and devices, as well as methods of producing and using same, which fully satisfy the objectives and advantages set forth hereinabove. Although the inventive concept(s) has been described in conjunction with the specific language set forth hereinabove, it is evident that many alternatives, modifications, and variations will be apparent to those skilled in the art. Accordingly, it is intended to embrace all such alternatives, modifications, and variations that fall within the spirit and broad scope of the presently disclosed and/or claimed inventive concept(s).

Examples of Using Calibration Fluids Comprising Pyrogallol as an Oxygen Scavenger to Produce Low Oxygen Concentrations in Bagged Reagents for the Calibration of on-Board Oxygen Sensors Referring now to the FIGURE, and more particularly to FIG. 1, shown therein is a graphical representation of blood gas analyzer calibration fluids comprising various percentages/concentrations of pyrogallol (x-axis) plotted against the partial pressures of oxygen ($pO_2$) produced within a zero-headspace pouch (measured in mmHg) for each particular percentage/concentration of pyrogallol present within the calibration fluid(s) (y-axis). As shown in FIG. 1, the oxygen response is inversely proportional to the amount of pyrogallol present within the calibration fluid—that is, the higher the amount of pyrogallol in the calibration fluid, the lower the partial pressure of oxygen of the calibration fluid within the zero headspace pouch.

As evidenced by FIG. 1, the partial pressure of oxygen measurements (in mmHg) indicates that increasing the percentage/concentration of pyrogallol within the calibration fluid reduces the oxygen response associated with the calibration fluid. As the percentage/concentration of pyrogallol is increased from 0.00% to 0.35% within the calibration fluid, the partial pressure of oxygen associated with the calibration fluid respectively decreases from about 27.5 mmHg within the zero headspace pouch to about 12.5 mmHg (thereby providing evidence regarding the inverse relationship between the amount of pyrogallol oxygen scavenger within the calibration fluid and the partial pressure of oxygen associated with the calibration fluid).

As discussed herein, the pyrogallol oxygen scavenger complexes with the oxygen present in the calibration and/or quality control reagent(s) to thereby reduce the levels of oxygen in the calibration fluid. As a result of increasing the concentration of the pyrogallol oxygen scavenger, the level of oxygen response is reduced to about zero (0) nano amperes, which directly correlates to a concentration of oxygen present in the calibration fluid of about zero (0). As a result, the calibration fluid is effective in setting the floor calibration measurement (i.e., a concentration of oxygen of about zero (0) for the effective calibration of at least one oxygen sensor present in a sensor array of a blood gas, electrolyte, and/or metabolite instrument. Accordingly, the pyrogallol oxygen scavenger accomplishes the objectives and advantages of the presently disclosed and/or claimed inventive concept(s).

Non-Limiting Examples of the Inventive Concept(s)

A calibration fluid for calibrating at least one $pO_2$ sensor of a blood gas, electrolyte, and/or metabolite instrument, comprising: at least one calibration and/or quality control reagent comprising oxygen; and a reagent comprising a pyrogallol oxygen scavenger, wherein a specific amount of the reagent comprising a pyrogallol oxygen scavenger is combined with the at least one calibration and/or quality control reagent comprising oxygen such that the pyrogallol oxygen scavenger complexes oxygen present in the at least one calibration and/or quality control reagent comprising oxygen to provide a desired oxygen concentration in the calibration fluid, and wherein the desired oxygen concentration is measured via at least one electrode.

The calibration, wherein the at least one calibration and/or quality control reagent comprising oxygen and the reagent comprising a pyrogallol oxygen scavenger are in aqueous solution.

The calibration fluid, wherein the at least one calibration and/or quality control reagent comprising oxygen and the reagent comprising a pyrogallol oxygen scavenger are disposed in a substantially air tight environment until use thereof.

The calibration fluid, wherein the pyrogallol oxygen scavenger comprises a concentration from about 0.05% to about 1% of the calibration fluid.

The calibration fluid, wherein the specific amount of the reagent comprising a pyrogallol oxygen scavenger is from about 0.1 milliliter to about 2 milliliters.

The calibration fluid, wherein the electrode is a bar metal electrode.

The calibration fluid, wherein the desired oxygen concentration comprises a partial pressure of oxygen of about zero millimeters of mercury (mmHg).

A method of calibrating at least one $pO_2$ sensor of a blood gas, electrolyte, and/or metabolite instrument, the method comprising the steps of: exposing at least one calibration and/or quality control reagent comprising oxygen to a specific concentration of a reagent comprising a pyrogallol oxygen scavenger to thereby form a calibration fluid, such exposure occurring immediately prior to the use of the calibration fluid, wherein the exposure is performed at a specific reaction temperature and for a specific amount of time, whereby the calibration fluid is thereby provided with a desired oxygen concentration based upon the concentration of the pyrogallol oxygen scavenger and the time and temperature of the exposure, and wherein the desired oxygen concentration is measured via at least one electrode of a sensor array, the senor array comprising the at least one electrode and at least one $pO_2$ sensor; and; contacting the calibration fluid having the desired oxygen concentration with the at least one $pO_2$ sensor of the sensor array.

The method, wherein the at least one calibration and/or quality control reagent comprising oxygen and the reagent comprising a pyrogallol oxygen scavenger are in aqueous solution.

The method, wherein the at least one calibration and/or quality control reagent comprising oxygen and the reagent comprising a pyrogallol oxygen scavenger are disposed in a substantially air tight environment until use thereof.

The method, wherein the pyrogallol oxygen scavenger comprises from about 0.05% to about 1% of the calibration fluid.

The method, wherein the specific reaction temperature if from about 20° C. to about 26° C.

The method, wherein the specific reaction time is from about 0.01 second to about 60 seconds.

The method, wherein the desired oxygen concentration comprises a partial pressure of oxygen of about zero millimeters of mercury (mmHg).

A kit for calibrating at least one $pO_2$ sensor of a blood gas, electrolyte, and/or metabolite instrument, the kit comprising: a calibration fluid, comprising: at least one calibration and/or quality control reagent comprising oxygen; and a reagent comprising a pyrogallol oxygen scavenger; and a sensor array comprising at least one electrode capable of measuring a desired concentration of oxygen in the calibration fluid, wherein, when calibration of the at least one $pO_2$ sensor is desired, a specific amount of the reagent comprising a pyrogallol scavenger is combined with the at least one calibration and/or quality control reagent comprising oxygen such that the pyrogallol oxygen scavenger complexes oxygen present in the at least one calibration and/or quality control reagent to provide the desired oxygen concentration in the calibration fluid, and wherein the desired oxygen concentration is measured via the at least one electrode of the sensor array prior to contacting the at least $pO_2$ sensor with the calibration fluid for calibration thereof.

The kit, wherein the at least one calibration and/or quality control reagent comprising oxygen and the reagent comprising a pyrogallol oxygen scavenger are in aqueous solution.

The kit, wherein the at least one calibration and/or quality control reagent comprising oxygen and the reagent comprising a pyrogallol oxygen scavenger are disposed in a substantially air tight environment until use thereof.

The kit, wherein the pyrogallol comprises a concentration from about 0.05% to about 1% of the calibration fluid.

The kit, wherein the specific amount of the reagent comprising a pyrogallol oxygen scavenger is from about 0.1 milliliter to about 2 milliliters.

The kit, wherein the electrode is a bar metal electrode.

The kit, wherein the desired oxygen concentration comprises a partial pressure of oxygen of about zero millimeters of mercury (mmHg).

Thus, in accordance with the presently disclosed and claimed inventive concept(s), there have been provided devices, kits, and methods for detecting at least one analyte present in a patient's low-volume liquid test sample. As described herein, the presently disclosed and claimed inventive concept(s) relate to embodiments of improved low-sample volume urinalysis assay strips for use in analyte(s) detection assay, as well as kits and methods of use related thereto. Such presently disclosed and/or claimed inventive concept(s) fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

The invention claimed is:

1. A method for monitoring the performance of a blood gas, electrolyte, and/or metabolite analyzer system, the method comprising the steps of:

(i) inserting a sensor cartridge into a blood gas, electrolyte, and/or metabolite instrument, the sensor cartridge comprising:

an amperometric sensor array comprising at least one sensor and at least one electrode, wherein the at least one sensor includes an amperometric partial pressure of oxygen ($pO_2$) sensor;

at least one calibration and/or quality control reagent; and aqueous pyrogallol;

(ii) activating the sensor cartridge to add aqueous pyrogallol to the at least one calibration and/or quality control reagent and incubating at a specific reaction temperature and for a specific reaction time sufficient to form at least one calibration and/or quality control fluid having a desired oxygen level, wherein the aqueous pyrogallol is added to the at least one calibration and/or quality control reagent in an amount that provides a concentration in a range of from about 0.05% to about 1% of the at least one calibration and/or quality control fluid; and (iii) contacting the at least one calibration and/or quality control fluid with the at least one electrode and the at least one sensor of the amperometric sensor array, wherein:

the at least one calibration and/or quality control fluid is contacted with the at least one electrode to directly determine a concentration of oxygen present therein based on an electrochemical current generated between the at least one electrode and oxygen present in the at least one calibration and/or quality control fluid, whereby the concentration of oxygen is directly proportional to the electrochemical current generated; and the at least one calibration and/or quality control fluid is contacted with the at least one sensor of the amperometric sensor array for calibration and/or quality control of the blood gas, electrolyte, and/or metabolite instrument.

2. The method of claim 1, wherein each of the at least one calibration and/or quality control reagent and the aqueous pyrogallol is separately disposed in a substantially air tight environment in the sensor cartridge until activation of the sensor cartridge.

3. The method of claim 1, wherein the aqueous pyrogallol is present in the calibration and/or quality control fluid at a concentration in a range of from about 0.05% to about 0.5%.

4. The method of claim 1, wherein in the activating step, the specific reaction temperature is in a range of from about 20° C. to about 26° C., and the specific reaction time is in a range of from about 0.01 second to about 60 seconds.

5. The method of claim 4, wherein the specific reaction time is in a range of from about 30 seconds to about 40 seconds.

6. The method of claim 1, wherein in the activating step, the desired oxygen level comprises a $pO_2$ of about zero millimeters of mercury (mmHg).

7. The method of claim 1, wherein the contacting step is performed within about 30 seconds of completion of the activating step.

8. The method of claim 1, wherein the sensor cartridge is further defined as a single-use sensor cartridge.

9. The method of claim 1, wherein the sensor cartridge is further defined as a multiple-use sensor cartridge.

10. The method of claim 9, further comprising repeating steps (ii) and (iii).

11. The method of claim 1, wherein the at least one electrode in the sensor cartridge is a bar metal electrode.

12. A method for monitoring the performance of a blood gas, electrolyte, and/or metabolite analyzer system, the method comprising the steps of:

(i) inserting a sensor cartridge into a blood gas, electrolyte, and/or metabolite instrument, the sensor cartridge comprising:

(a) an amperometric sensor array comprising at least one sensor and at least one electrode, wherein the at least one sensor includes an amperometric partial pressure of oxygen ($pO_2$) sensor;

(b) a first calibration and/or quality control reagent;

(c) a second calibration and/or quality control reagent having a $pO_2$ value above zero millimeters of mercury (mmHg);

(d) aqueous pyrogallol; and wherein each of (b), (c), and (d) is separately disposed in a substantially air tight environment in the sensor cartridge until activation of the sensor cartridge;

(ii) activating the sensor cartridge to add aqueous pyrogallol to the first calibration and/or quality control reagent and incubating at a specific reaction temperature and for a specific reaction time sufficient to form a first calibration and/or quality control fluid having a desired oxygen level;

(iii) contacting the first calibration and/or quality control fluid with the amperometric sensor array, wherein an electrochemical current is generated between the at least one electrode of the amperometric sensor array and oxygen present in the calibration and/or quality control fluid, whereby the concentration of oxygen is directly proportional to the electrochemical current generated, and wherein the first calibration and/or quality control fluid sets a floor calibration measurement of the at least one $pO_2$ sensor; and (iv) contacting the second calibration and/or quality control reagent with the amperometric sensor array, wherein the second calibration and/or quality control reagent sets a ceiling calibration measurement of the at least one $pO_2$ sensor.

13. The method of claim 12, wherein the second calibration and/or quality control reagent has a $pO_2$ value of about 160 mmHg, and wherein the desired oxygen level generated in the first calibration and/or quality control fluid comprises a $pO_2$ value of about 0 mmHg.

14. The method of claim 12, wherein in the activating step, the aqueous pyrogallol is present in the first calibration and/or quality control fluid at a concentration in a range of from about 0.05% to about 1%.

15. The method of claim 12, wherein in the activating step, the specific reaction temperature is in a range of from about 20° C. to about 26° C., and the specific reaction time is in a range of from about 0.01 second to about 60 seconds.

16. The method of claim 12, wherein step (iii) is performed within about 30 seconds of completion of step (ii).

17. A method for monitoring the performance of a blood gas, electrolyte, and/or metabolite analyzer system, the method comprising the steps of:

(i) inserting a sensor cartridge into a blood gas, electrolyte, and/or metabolite instrument, the sensor cartridge comprising:

an amperometric sensor array comprising at least one sensor and at least one electrode, wherein the at least one sensor includes an amperometric partial pressure of oxygen ($pO_2$) sensor;

a first calibration and/or quality control reagent;

a second calibration and/or quality control reagent having a $pO_2$ value above zero millimeters of mercury (mmHg);

a third calibration and/or quality control reagent having a $pO_2$ value above zero mmHg; and aqueous pyrogallol; and (ii) activating the sensor cartridge to add aqueous pyrogallol to the first calibration and/or quality control reagent and incubating at a specific reaction temperature and for a specific reaction time sufficient to form a first calibration and/or quality control fluid having a $pO_2$ value of about 0 mmHg;

(iii) activating the sensor cartridge to add aqueous pyrogallol to the third calibration and/or quality control reagent and incubating at a specific reaction temperature and for a specific reaction time sufficient to form a third calibration and/or quality control fluid having a $pO_2$ value between 0 mmHg and the $pO_2$ value of the second calibration and/or quality control reagent;

(iv) contacting the first calibration and/or quality control fluid with the amperometric sensor array, wherein an electrochemical current is generated between the at least one electrode of the amperometric sensor array and oxygen present in the calibration and/or quality control fluid, whereby the concentration of oxygen is directly proportional to the electrochemical current generated, and wherein the first calibration and/or quality control fluid sets a floor calibration measurement of the at least one $pO_2$ sensor;

(v) contacting the second calibration and/or quality control reagent with the amperometric sensor array, wherein the second calibration and/or quality control reagent sets a ceiling calibration measurement of the at least one $pO_2$ sensor; and (vi) contacting the third calibration and/or quality control fluid with the amperometric sensor array, wherein the third calibration and/or quality control fluid sets a calibration measurement of the at least one $pO_2$ sensor between the floor and ceiling measurements.

18. The method of claim 17, wherein the second calibration and/or quality control reagent has a $pO_2$ value of about 160 mmHg, and wherein in step (iii), the desired $pO_2$ value generated in the third calibration and/or quality control fluid is in a range between 0 mmHg and 160 mmHg.

19. The method of claim 17, wherein at least one of:

in step (ii), the aqueous pyrogallol is present in the first calibration and/or quality control fluid at a concentration in a range of from about 0.05% to about 1%;

in steps (ii) and (iii), the specific reaction temperature is in a range of from about 20° C. to about 26° C., and the specific reaction time is in a range of from about 0.01 second to about 60 seconds; and/or step (iv) is performed within about 30 seconds of completion of step (ii), and step (vi) is performed within about 30 seconds of completion of step (iii).

* * * * *